United States Patent [19]

Stewart

[11] Patent Number: 5,356,391
[45] Date of Patent: Oct. 18, 1994

[54] FLEXIBLE RETAINER FLANGE FOR GASTROSTOMY TUBE AND THE METHOD OF INSTALLING IT

[75] Inventor: Daren L. Stewart, Redwood City, Calif.

[73] Assignee: Medical Innovations Corp., Milpitas, Calif.

[21] Appl. No.: 901,894

[22] Filed: Jun. 22, 1992

[51] Int. Cl.⁵ .............................................. A61M 5/32
[52] U.S. Cl. ................................. 604/175; 604/174; 128/DIG. 26
[58] Field of Search .................... 604/49, 54, 104, 105, 604/174, 175, 264, 280; 128/DIG. 26

[56] References Cited

U.S. PATENT DOCUMENTS

| | | | |
|---|---|---|---|
| 3,915,171 | 10/1975 | Shermeta | 604/104 X |
| 4,393,873 | 7/1983 | Nawash et al. | 604/151 |
| 4,685,901 | 8/1987 | Parks | 604/96 |
| 4,717,385 | 1/1988 | Cameron et al. | 604/174 |
| 4,808,162 | 2/1989 | Oliver | 604/180 |
| 4,834,712 | 5/1989 | Quinn et al. | 604/175 |
| 4,863,438 | 9/1989 | Gauderer et al. | 604/247 |
| 4,900,306 | 2/1990 | Quinn et al. | 604/97 |
| 4,944,732 | 7/1990 | Russo | 604/247 |
| 5,007,900 | 4/1991 | Picha et al. | 604/106 |
| 5,073,166 | 12/1991 | Parks et al. | 604/174 X |
| 5,080,650 | 1/1992 | Hirsch et al. | 604/104 |
| 5,112,310 | 5/1992 | Grobe | 604/175 |

Primary Examiner—John D. Yasko
Assistant Examiner—Corrine Maglione
Attorney, Agent, or Firm—Workman, Nydegger, Jensen

[57] ABSTRACT

A gastrostomy tube having a collapsible, internal retention flange is disclosed, and the gastrostomy tube is inserted into a patient's stomach by a percutaneous endoscopic or other suitable technique. The internal retention flange comprises a dome shape that will not only reduce patient risk during the placement procedure, but will also allow for a more consistent and less traumatic external removal procedure.

17 Claims, 1 Drawing Sheet

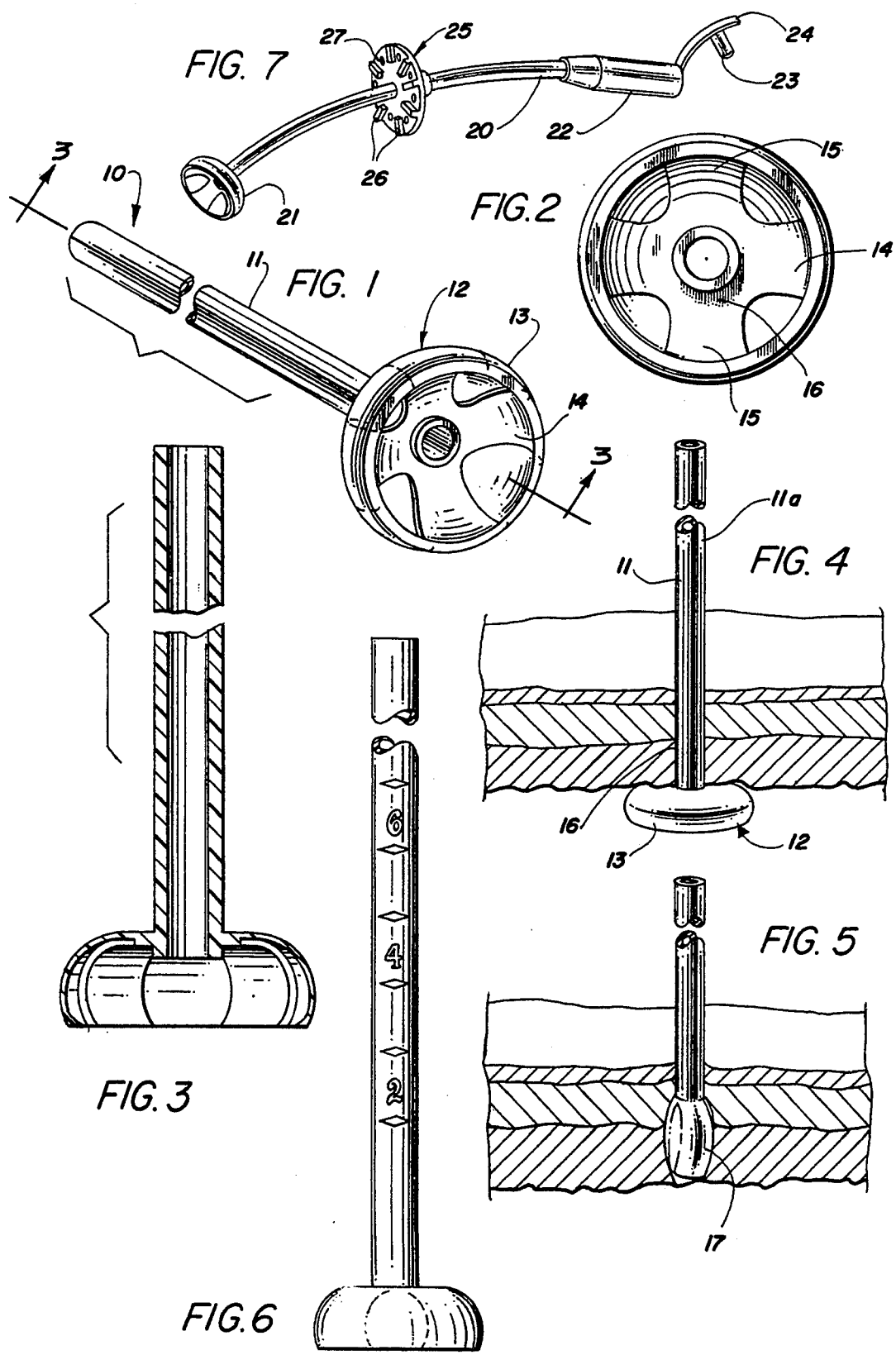

FLEXIBLE RETAINER FLANGE FOR GASTROSTOMY TUBE AND THE METHOD OF INSTALLING IT

BACKGROUND OF THE INVENTION

This invention relates to a new and improved gastrostomy device with a flexible, collapsible internal retention dome. This retention dome improves the ease of insertion by collapsing down in size as the gastrostomy device is pulled down the esophagus of a patient during a placement procedure. The collapsibility of the retention dome also reduces the risk of tissue and stoma damage, and reduces patient trauma during a subsequent external traction removal procedure.

Various types of gastrostomy devices have been installed in patients by means of a percutaneous insertion, a surgical placement, a radiological placement or others. The procedures employed generally follow those known as the Sachs-Vine procedure, the Gauderer and Ponsky procedure, and others. Typical patents describing these procedures and publications of the technique are set forth in U.S. Pat. Nos. 4,861,334; 4,900,306; and 5,080,650.

Once installed, these devices are retained in place by an internal retention member. Various types of these internal retention members currently exist, one type being a molded or permanently attached flange element, and another type being a collar and balloon.

Removal of gastrostomy devices is needed upon conclusion of enteral nutrition of a patient, or if the device were to be replaced with another enteral feeding device (e.g. an inflatable, replaceable gastrostomy tube), and various techniques are currently used for this removal procedure. These techniques include 1. cutting the gastrostomy tube at skin level and retrieving the bumper endoscopically; 2. cutting the gastrostomy tube at skin level and allowing the flange or collar to pass through the gastro-intestinal tract and be expelled by excretion; or, 3. physically pulling the internal retention device through the patient's stoma.

There are problems associated with all three of the above prior art removal techniques. For example, the endoscopic retrieval process places the patient at high risk during the procedure. Some of the risks involved are esophageal tissue damage and possible blockage of the trachea by the flange or collar upon retraction which could result in death.

Another risk occurs in allowing the flange or collar to pass through the gastrointestinal tract which may cause intestinal or bowel blockage.

Still another risk arises when these prior art devices are removed from a patient by means of external traction techniques, since they have been known to cause considerable trauma and excessive bleeding to patients.

Consequently, the device of the present invention is designed for placement by either of the aforementioned percutaneous endoscopic or other types of procedures, and improves upon prior art devices during placement of the device and also during the external traction removal procedure.

THE INVENTION

According to the invention, a gastrostomy device is disclosed which may be inserted into a patient by a percutaneous endoscopic, radiological, surgical, or other type of procedure. The device comprises a catheter tube, a proximal portion of which is used as a means for insertion, and a distal internal retention flange.

The internal retention flange includes a dome which is designed to collapse down significantly in diameter when a force is longitudinally applied along the axis of the catheter tube. The collapsing aspect of this dome allows for easier passage during placement of the device.

In normal catheter operation, the shape of the dome enables it to conform to the contour of the patient's stomach and provide a comfortable and secure internal retention means. When the gastrostomy device is no longer needed by the patient, or when replacement and substitution is required by another enteral feeding device, the collapsing dome of the retainer facilitates the external traction removal procedure.

The shape and configuration of the dome, as described herein, enables the dome to plicate when a force is applied longitudinally along the axis of the catheter tube. Hence, the dome will collapse uniformly from the periphery to the central portion.

The predictable manner in which this dome buckles under a reduced amount of force is directly related to the varying thicknesses that are designed into the dome. The buckling or collapsing effect, and the compact shape which the dome assumes during removal of the gastrostomy tube, can alleviate much of the pain and trauma associated with this procedure.

IN THE DRAWINGS

FIG. 1 is an external, perspective view of the gastrostomy device of this invention;

FIG. 2 is a bottom plan view of FIG. I showing the underside of the flange element;

FIG. 3 is a sectional view in side elevation taken along lines 3—3 of FIG. 1;

FIG. 4 is an external view in side elevation and partly in perspective showing the gastrostomy tube of this invention following installation into a patient;

FIG. 5 is an external view in side elevation, partly in perspective, showing the gastrostomy tube of this invention as it is being withdrawn from a patient;

FIG. 6 is an external view in side elevation showing indicia markings on the exterior of the catheter; and, FIG. 7 is an external view, partly in perspective of another embodiment of this invention.

DESCRIPTION OF THE PREFERRED EMBODIMENTS

The gastrostomy device 10 of this invention is shown in FIG. 1, and comprises a hollow elongate catheter tube 11, through which a patient is fed, and an attached flange 12 at the distal end. The flange may be attached to the catheter tube by heat sealing, adhesives, sonic bonding, etc., or the flange 12 may be integrally formed with the catheter.

The flange and catheter components are constructed of a biocompatible polymer such as a silicone elastomer, silicone copolymer, polyurethane, etc. Either of these two components may incorporate a white filler, or may omit a filler and be relatively clear. Also, a radiopaque material such as $BaSO_4$ may be incorporated into the distal end of the catheter. As shown in FIG. 6, spacing indicia are provided to enable location of the device during installation, and during use.

Typically, the catheter has a durometer hardness of about 40-60, with an outside diameter of about 14-20

French, an inside diameter of about 155–175 mils, and a wall thickness of about 40–60 mils.

A dilating sheath of polyethylene, or ABS (not shown) is attached to the end of the catheter to enable manipulation of the device during installation. Alternatively, a wire loop (not shown) may be used with a dilating tip, and the wire is typically made of a medical grade stainless steel and coated with a biocompatible material such as a polyurethane.

Due to its plastic memory, in its usual or unconstrained form, the flange 12 comprises an approximately hemispherically shaped dome 13. The dome is about 20–35 mils thick and is reinforced with a cut-out 14 about 20–25 mils thick and positioned on the inside of the dome. The cut-out 14 has a cruciform shape which defines four elements 15 spaced equally around the interior of the hemisphere dome. The central area 16 of the cut-out is continuous, and the dome reinforcement in this central area is about 40–60 mils thick. The cut-out 14 may be formed integrally while being insert molded, or it may be formed separately and then attached to the dome by heat or adhesive sealing, sonic bonding, etc.

It will be appreciated that the cruciform shape of the cut-out 14 is not critical, and the cut-out may assume various shapes, such as elliptical, rectangular, triangular, asterism, striated, etc., provided it enables collapse of the hemisphere dome from the periphery to the central area 16 during removal of the gastrostomy device.

As shown in FIGS. 4 and 5, a portion 11a of the catheter extends beyond the patient and will engage a closure member (not shown), which when opened, connects to a feeding port; this type of arrangement is well known in the art.

If desired, the external portion of the catheter can be formed into a feeding port which functions along with a gasket to produce a sliding friction fit and thereby accommodate for peristaltic forces and other stomach movements. U.S. Pat. Nos. 4,666,433; 4,685,901; 4,701,163; and, 4,798,592 to Applicant's assignee, and incorporated herein by reference, show this arrangement. This embodiment shown in FIG. 7 provides a catheter 20 attached at one end to a dome element 21 of this invention, and includes a feeding port 22 mounted at the opposite end of the catheter. A closure plug 23 attached to a connector 24 fits into the feeding port when the device is not in use.

A gasket 25 provides a sliding friction fit along the catheter and moves outwardly along the catheter in response to peristaltic forces, stomach movements, etc., and to prevent the device from being drawn into the patient's stomach. Gasket 25 has a plurality of legs 26 which rest against the user's body, and along with a plurality of air vent bores 27, permit better air circulation and reduce the presence of moisture.

Generally speaking a size differential of about 10–20 mils between the outside diameter of the catheter and the inside diameter of the gasket bore is employed to produce a sliding friction fit between the gasket and catheter.

FIGS. 4 and 5 illustrate the gastrostomy tube 10 when installed through a stoma 16 of a patient as shown in FIG. 4, and during commencement of its removal, shown in FIG. 5. When installed, as shown in FIG. 4, the gastrostomy tube permits feeding through the catheter 11, while being retained within the stomach of the patient by means of the flange 12. The retention characteristics of the present gastrostomy tube in the patient are quite adequate. When the gastrostomy tube 10 is retracted, usually for replacement purposes, the flange commences to collapse 17 as the retraction begins, and this initial collapse can be felt by the health care worker, physician, etc., who perform the procedure. Hence, following this initial collapse, less subsequent force compared to prior art devices, is required to pull the gastrostomy device from the patient's body.

Removal of these prior art devices from the patient frequently results in trauma, and often requires the use of masks and/or other coverings by medical workers when performing this procedure. The gastrostomy device of the present invention is less painful and traumatic to the patient during its removal, and is less troublesome to health care workers.

I claim:

1. A gastrostomy tube comprising:
   a catheter member comprising a distal end for placement within a patient's stomach, and a proximal end extending outside of the patient to provide access for feeding the patient through the catheter member; and
   a dome-shaped flange means mounted to the distal end within the stomach and having a first diameter for retaining the gastrostomy tube in place within the stomach of the patient, the dome-shaped flange means comprising a sufficiently resilient and flexible reinforcing means for collapsing the dome-shaped flange means upon itself to form a second diameter smaller than the first diameter so as to become elongated in form to permit passage of the dome-shaped flange means through a body opening without the aid of an insertion and removal tool when the dome-shaped flange means is drawn through a body opening having a diameter less than the first diameter in response to a traction force applied to the catheter member.

2. The gastrostomy device of claim 1, in which the dome-shaped flange means is secured to the catheter by one of adhesives, heat sealing, sonic bonding, or by being integrally formed therewith.

3. The gastrostomy device of claim 1, in which the reinforcing means comprises a reinforcement member having a shape including cruciform, elliptical, triangular, rectangular, striated, and asterism.

4. The gastrostomy device of claim 3, in which the reinforcement member is formed on the dome-shaped flange means by one of heat sealing, adhesive sealing, sonic bonding and integrally forming by injection molding.

5. The gastrostomy device of claim 3, in which the dome-shaped flange means is about 20–35 mils thick, the reinforcement member is about 20–25 mils thick, and a central area of the dome-shaped flange means is about 40–60 mils thick.

6. The gastrostomy device of claim 1, in which the dome-shaped flange means and catheter member are constructed of a biocompatible polymer selected from the class consisting of a silicone elastomer, silicone copolymer and polyurethane.

7. The gastrostomy tube of claim 1, providing an extension of the catheter member from the patient, a feeding port being mounted on the extension, and a gasket mounted along the catheter member, and forming a sliding friction fit therewith to accommodate for peristaltic expansion and stomach movements, and to prevent the catheter member from being drawn into the patient.

8. A gastrostomy tube comprising:

a catheter member comprising a distal end for placement within a patient's stomach, and a proximal end extending outside of the patient to provide access for feeding the patient through the catheter member; and a flange means mounted at the distal end of the catheter member for retaining the gastrostomy tube in place within the stomach of the patient, the flange means comprising a flexible thin-walled retention dome member having an approximately hemispherical shape, and being reinforced by a reinforcing member completely joined to a surface of the dome member, and the reinforcing member having a shape that together with the dome member defines a first thickened central portion, and remaining portions of the dome ember without the reinforcing member defining other thinner, peripheral portions, the flange means and catheter member being constructed of a biocompatible polymer, and the other thinner peripheral portions of the dome ember causing the dome member to collapse upon itself so as to form an elongate shape without the aid of an insertion and removal tool when passing through a body opening smaller than the uncollapsed dome member during placement or removal of the gastrostomy tube, and the first thickened central portion causing the dome member to expand from its collapsed shape back to its hemispherical shape solely due to its flexibility and without requiring the use of a tool after passing completely through the body opening, so as to thereafter conform to the patient's stomach, and thereby securing the gastrostomy tube in place therein.

9. The gastrostomy device of claim 8, in which the biocompatible polymer is selected from the class consisting of: silicone elastomer, silicone copolymer and polyurethane.

10. A method of installing a gastrostomy tube, the gastrostomy tube comprising:
   a.) a catheter member for positioning within a patient's stomach, the catheter defining distal and proximal ends, the proximal end extending from the patient for attachment to a feeding means; and,
   b.) a flange mounted at the distal end of the catheter for retaining the gastrostomy tube in place in the patient, the flange defining a flexible, thin-walled retention dome structure having an approximately hemispherical shape, and being stabilized by a reinforcement, positioned thereon, the dome and reinforcement defining a thickened central portion on the dome and a thinner, partially reinforced peripheral portion, the thin-walled structure having an approximately hemispherical shape, and being stabilized by a reinforcement, positioned thereon, the dome and reinforcement defining a thickened central portion on the dome and a thinner, partially reinforced peripheral portion, the thin-walled structure of the dome causing the dome to collapse to a compact shape during placement of the gastrostomy tube, the method comprising:
   i. placing the gastrostomy tube in the patient's stomach, and in an initial position, collapsing the dome during placement of the gastrostomy tube;
   ii. securing the gastrostomy tube within the patient's stomach during use, by expanding the dome from its collapsed position during placement to maintain its hemispherical shape, solely due to its plastic memory, and without requiring use of a tool, and conforming the dome to the patient's stomach; and,
   iii. removing the gastrostomy tube from the patient's stomach, collapsing the dome in a uniform manner from its peripheral portion to the central portion within the stoma, due to the thin-walled structure of the dome, thereby facilitating removal of the gastrostomy tube solely by an external traction force applied longitudinally along the axis of the catheter tube, without requiring use of a removal tool, with reduced pain and trauma to the patient.

11. The method of claim 10, in which during removal of the gastrostomy from the patient, an initial collapse of the flange occurs, and this initial collapse can be felt by a health care worker, thereby enabling less subsequent force to be applied to the gastrostomy tube during the remaining portion of the removal procedure.

12. The method of claim 11, in which the flange is secured to the catheter by one of heat sealing, adhesives, sonic bonding, or by integrally forming by insert molding.

13. The method of claim 12, in which the reinforcement has a shape including, cruciform, elliptical, rectangular, triangular, striated and asterism.

14. The method of claim 13, in which the reinforcement is formed on the dome by one of heat sealing, adhesive sealing, sonic bonding and integrally forming by insert molding.

15. The method of claim 14, in which the dome is about 20–35 mils thick, the reinforcement about 20–25 mils thick, and the dome central area is about 40–60 mils thick.

16. The method of claim 15, in which the flange and catheter are constructed of a biocompatible polymer selected from the class consisting of a silicone elastomer, silicone copolymer, and polyurethane.

17. The method of claim 10, providing an extension of the catheter from the patient, a feeding port being mounted on the extension, and a gasket mounted along the catheter, and forming a sliding friction fit therewith to accommodate for peristaltic expansion and stomach movements, and to prevent the catheter from being drawn into the patient.

* * * * *

UNITED STATES PATENT AND TRADEMARK OFFICE
CERTIFICATE OF CORRECTION

PATENT NO. : 5,356,391
DATED : October 18, 1994
INVENTOR(S) : DAREN L. STEWART

It is certified that error appears in the above-indentified patent and that said Letters Patent is hereby corrected as shown below:

Column 5, line 21, "ember" should be --member--

Column 5, line 53 to column 6, line 2, delete "having an approximately hemispherical shape, and being stabilized by a reinforcement, positioned thereon, the dome and reinforcement defining a thickened central portion on the dome and a thinner, partially reinforced peripheral portion, the thin-walled structure"

Signed and Sealed this

Sixteenth Day of May, 1995

Attest:

BRUCE LEHMAN

*Attesting Officer*    Commissioner of Patents and Trademarks